(12) United States Patent
Bui et al.

(10) Patent No.: US 10,028,849 B2
(45) Date of Patent: *Jul. 24, 2018

(54) FLEXIBLE STENT GRAFT

(71) Applicant: Cook Medical Technologies LLC, Bloomington, IN (US)

(72) Inventors: Bao Bui, Sherbrooke (CA); Werner D. Ducke, Queensland (AU); David E. Hartley, Wannanup (AU); Raymond B. Leonard, II, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 282 days.

This patent is subject to a terminal disclaimer.

(21) Appl. No.: 14/807,278

(22) Filed: Jul. 23, 2015

(65) Prior Publication Data

US 2015/0320578 A1    Nov. 12, 2015

Related U.S. Application Data

(63) Continuation of application No. 12/261,860, filed on Oct. 30, 2008, now Pat. No. 9,107,741.

(60) Provisional application No. 61/126,801, filed on May 6, 2008, provisional application No. 61/065,942, filed on Feb. 15, 2008, provisional application No. 61/001,480, filed on Nov. 1, 2007.

(51) Int. Cl.
*A61F 2/06* (2013.01)
*A61F 2/856* (2013.01)
*A61F 2/07* (2013.01)
*A61F 2/88* (2006.01)
*A61F 2/89* (2013.01)

(52) U.S. Cl.
CPC .............. *A61F 2/856* (2013.01); *A61F 2/07* (2013.01); *A61F 2/88* (2013.01); *A61F 2/89* (2013.01); *A61F 2002/072* (2013.01); *A61F 2002/075* (2013.01); *A61F 2230/0069* (2013.01); *A61F 2250/0018* (2013.01)

(58) Field of Classification Search
CPC ........ A61F 2/07; A61F 2002/075; A61F 2/88; A61F 2220/0075; A61F 2250/0039
USPC .......... 623/1.13, 1.15, 1.16, 1.22, 1.28, 1.35
See application file for complete search history.

(56) References Cited

U.S. PATENT DOCUMENTS

| | | | |
|---|---|---|---|
| 4,842,575 A | 6/1989 | Hoffman, Jr. et al. |
| 5,725,547 A | 3/1998 | Chuter |
| 6,494,904 B1 | 12/2002 | Love |
| 6,565,596 B1 | 5/2003 | White et al. |
| 7,232,459 B2 | 6/2007 | Greenberg et al. |

(Continued)

FOREIGN PATENT DOCUMENTS

| | | |
|---|---|---|
| EP | 1360942 A1 | 11/2003 |
| JP | 2001-504023 | 3/2001 |

(Continued)

OTHER PUBLICATIONS

Patent Examination Report No. 1 for corresponding Australian Application No. 2008319288, dated Feb. 1, 2013, 5 pages.

(Continued)

*Primary Examiner* — Katherine M Shi
(74) *Attorney, Agent, or Firm* — Brinks Gilson & Lione

(57) ABSTRACT

A flexible stent graft for deployment in a body vessel at a treatment site that includes a tubular body of graft material having circumferential crimps with alternative troughs and (Continued)

crests along its length, and a stent system comprising a plurality of circumferential turns which are attached at the crest.

15 Claims, 11 Drawing Sheets

(56) References Cited

U.S. PATENT DOCUMENTS

| | | |
|---|---|---|
| 7,846,194 B2 | 12/2010 | Hartley et al. |
| 7,998,186 B2 | 8/2011 | Hartley |
| 7,998,187 B2 | 8/2011 | Hartley et al. |
| 8,012,193 B2 | 9/2011 | Hartley et al. |
| 8,021,412 B2 | 9/2011 | Hartley et al. |
| 8,449,600 B2 | 5/2013 | Hartley et al. |
| 2003/0040803 A1 | 2/2003 | Rioux et al. |
| 2003/0130721 A1 | 7/2003 | Martin et al. |
| 2003/0195609 A1 | 10/2003 | Berenstein et al. |
| 2003/0199967 A1 | 10/2003 | Hartley et al. |
| 2003/0208256 A1 | 11/2003 | DiMatteo et al. |
| 2003/0212450 A1 | 11/2003 | Schlick |
| 2003/0233140 A1 | 12/2003 | Hartley et al. |
| 2005/0113905 A1 | 5/2005 | Greenberg et al. |
| 2005/0131516 A1 | 6/2005 | Greenhalgh |
| 2005/0182481 A1 | 8/2005 | Schlick et al. |
| 2006/0004433 A1 | 1/2006 | Greenberg et al. |
| 2006/0247761 A1 | 11/2006 | Greenberg et al. |
| 2008/0114445 A1 | 5/2008 | Melsheimer et al. |
| 2008/0288047 A1 | 11/2008 | Friebe et al. |
| 2010/0152833 A1 | 6/2010 | Burnside et al. |

FOREIGN PATENT DOCUMENTS

| | | |
|---|---|---|
| JP | 2003-250880 | 9/2003 |
| JP | 2003-325674 | 11/2003 |
| WO | WO 98/27893 A2 | 7/1998 |
| WO | WO 98/27893 A3 | 7/1998 |
| WO | WO 01/52770 A1 | 7/2001 |
| WO | WO 2006/034276 A1 | 3/2006 |
| WO | WO 2006/130755 A2 | 12/2006 |
| WO | WO 2007/039273 A1 | 4/2007 |
| WO | WO 2008/050115 A1 | 5/2008 |

OTHER PUBLICATIONS

Office Action for corresponding EP 08844695.0, dated Oct. 10, 2011, 5 pages.
Office Action for corresponding EP 08844695.0, dated Jan. 20, 2014, 5 pages.
Office Action and translation for corresponding Japanese Application No. 2010-532062, dated Oct. 8, 2013, 4 pages.
Office Action and translation for corresponding Japanese Application No. 2010-532062, dated Mar. 5, 2013, 7 pages.
International Search Report and Written Opinion for corresponding Application No. PCT/US2008/012381, dated Feb. 26, 2009.
International Preliminary Report on Patentability for corresponding Application No. PCT/US2008/012381, dated May 4, 2010, 8 pages.

Fig. 1
Fig. 1A
Fig. 2
Fig. 3
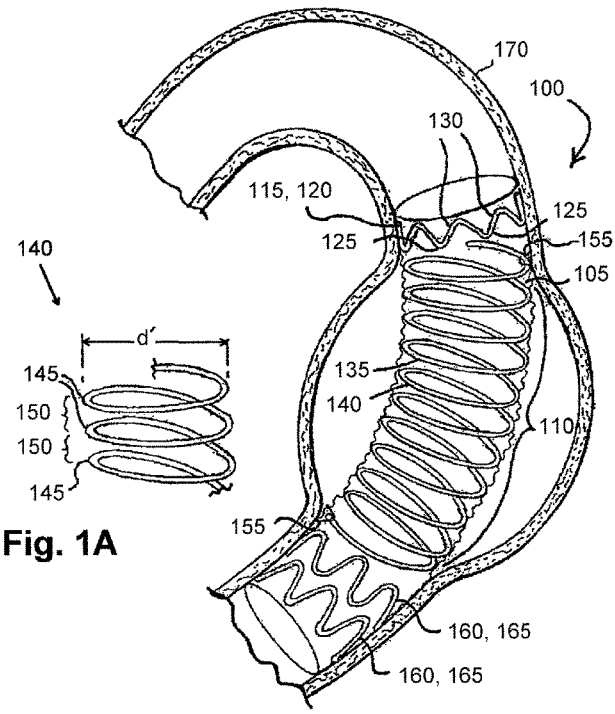
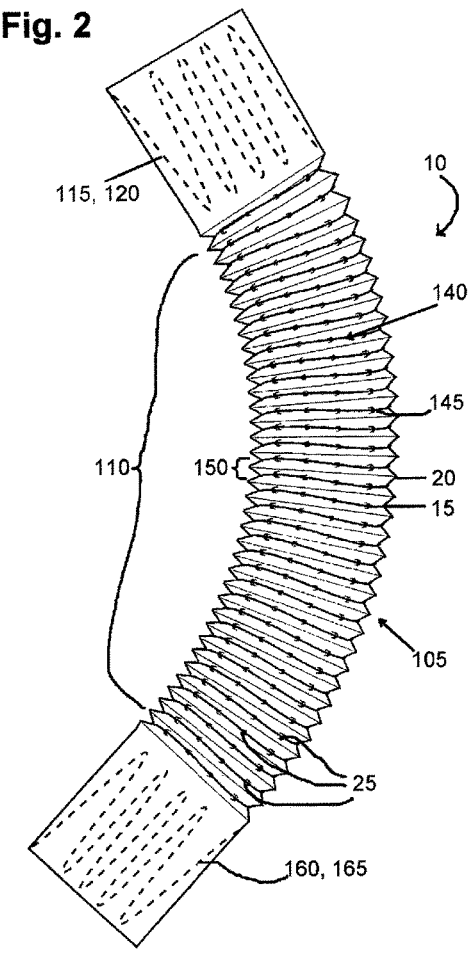
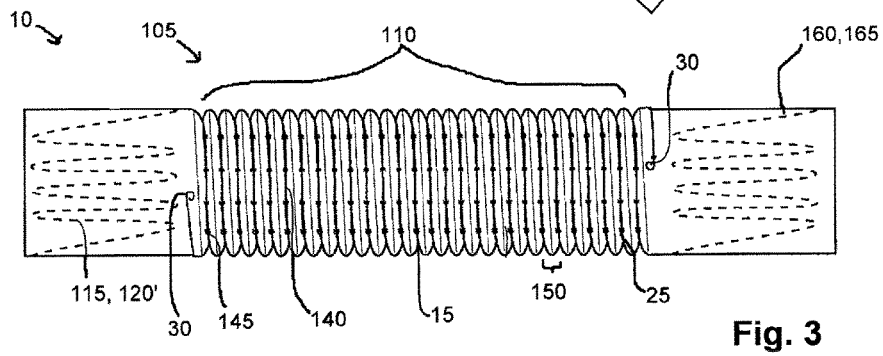

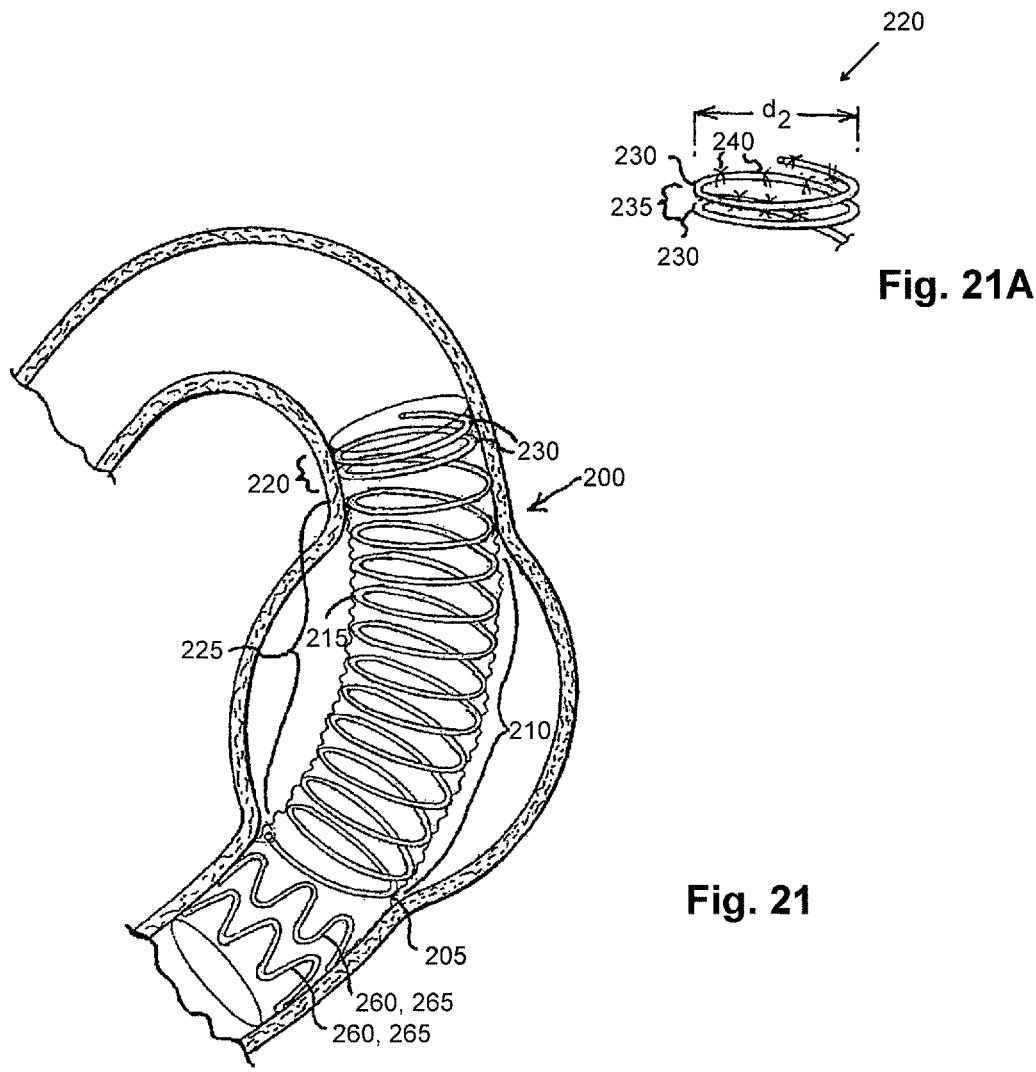
Fig. 21A
Fig. 21
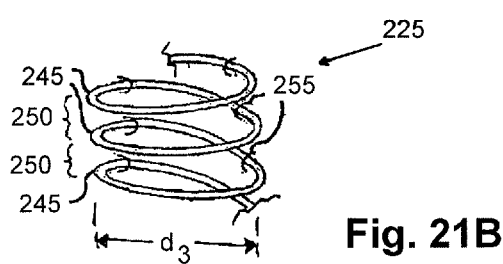
Fig. 21B

FLEXIBLE STENT GRAFT

RELATED APPLICATIONS

This application is a continuation of U.S. patent application Ser. No. 12/261,860 filed Oct. 30, 2008, claims priority and the benefit of the filing date under 35 U.S.C. § 119(e) of U.S. Provisional Patent Application Ser. No. 61/126,801, filed May 6, 2008, U.S. Provisional Patent Application Ser. No. 61/065,942, filed Feb. 15, 2008, and U.S. Provisional Patent Application Ser. No. 61/001,480, filed Nov. 1, 2007, all of which are hereby incorporated by reference in their entirety.

TECHNICAL FIELD

The present disclosure relates generally to medical devices and more particularly to endovascular devices.

BACKGROUND

Aneurysms occur in blood vessels at sites where, due to age, disease or genetic predisposition of the patient, the strength or resilience of the vessel wall is insufficient to prevent ballooning or stretching of the wall as blood passes through. If the aneurysm is left untreated, the blood vessel wall may expand and rupture, often resulting in death.

To prevent rupturing of an aneurysm, a stent graft may be introduced into a blood vessel percutaneously and deployed to span the aneurysmal sac. Stent grafts include a graft fabric secured to a cylindrical scaffolding or framework of one or more stents. The stent(s) provide rigidity and structure to hold the graft open in a tubular configuration as well as the outward radial force needed to create a seal between the graft and a healthy portion of the vessel wall. Blood flowing through the vessel can be channeled through the hollow interior of the stent graft to reduce, if not eliminate, the stress on the vessel wall at the location of the aneurysmal sac. Stent grafts may reduce the risk of rupture of the blood vessel wall at the aneurysmal site and allow blood to flow through the vessel without interruption.

Aneurysms occurring in the aorta, the largest artery in the human body, may occur in the chest (thoracic aortic aneurysm) or in the abdomen (abdominal aortic aneurysm). Due to the curvature of the aortic arch, thoracic aortic aneurysms can be particularly challenging to treat. Other parts of the vasculature, such as the common iliac artery which extends from the aorta, can also be extremely tortuous. Hence, a stent graft deployed into such regions is preferably able to conform to the vasculature.

SUMMARY

A flexible stent graft for deployment in a body vessel at a treatment site is described. The stent graft is particularly suited for use in the thoracic aorta for the treatment of an aortic aneurysm or dissection. The stent graft also may be advantageous for use in other curved vessels, such as the common iliac artery. The stent graft may change in length or curvature as needed, thus providing size and positioning flexibility during deployment and accommodating changes in the vessel after implantation.

The flexible stent graft includes, according to one embodiment, a tubular body, at least a first portion of which comprises a graft material and a coiled stent comprising a plurality of helical turns with spacings between the turns. The coiled stent is affixed to the graft material of the first portion. The first portion has a first portion diameter and the coiled stent has a helix diameter which is substantially the same as the first portion diameter. The coiled stent comprises a ratio of helical pitch to helix diameter of from about 1:2 to about 1:20, where the helical pitch is the spacing between adjacent turns of the coiled stent.

The flexible stent graft includes, according to another embodiment, a graft material forming a generally tubular body having a proximal end, a distal end, and a slackened central portion between the ends, and a stent framework secured to the graft material. The stent framework includes one or more proximal sealing stents disposed at the proximal end of the generally tubular body. The stent framework also includes a flexing stent having a coiled configuration including a plurality of helical turns disposed distally adjacent to the one or more proximal sealing stents and radially adjacent to the slackened central portion of the tubular body. The slackened central portion is configured to accommodate a change in length or configuration of the flexing stent.

The flexible stent graft includes, according to another embodiment, a graft material forming a generally tubular body having a proximal end, a distal end, and a slackened central portion between the ends, and a stent framework secured to the graft material. The stent framework includes a coiled stent extending from the proximal end of the generally tubular body along the slackened central portion thereof. The coiled stent includes a sealing portion having helical turns of a first spacing and a flexing portion having helical turns of a second spacing larger than the first spacing. The slackened central portion is configured to accommodate a change in length or configuration of the flexing portion of the coiled stent.

Other systems, methods, features and advantages will be, or will become, apparent to one with skill in the art upon examination of the following figures and detailed description. It is intended that all such additional systems, methods, features and advantages be included within this description, be within the scope of the invention, and be protected by the following claims.

BRIEF DESCRIPTION OF THE DRAWINGS

The system may be better understood with reference to the following drawings and description. Components shown in the figures are intended to illustrate principles of the invention and are not necessarily drawn to scale. Moreover, in the figures, like referenced numerals designate corresponding parts throughout the different views.

FIG. 1 shows a first embodiment of a stent graft in a deployed configuration in the descending thoracic aorta;

FIG. 1A shows a close-up view of a portion of the stent graft of FIG. 1.

FIG. 2 shows an alternative of the first embodiment of a stent graft in a curved configuration;

FIG. 3 shows the stent graft of FIG. 2 in a straight configuration;

FIG. 21 shows a stent graft according to a second embodiment in a deployed configuration in the descending thoracic aorta;

FIGS. 21A-21B show close-up views of portions of the stent graft of FIG. 21;

DETAILED DESCRIPTION

Figure 4:
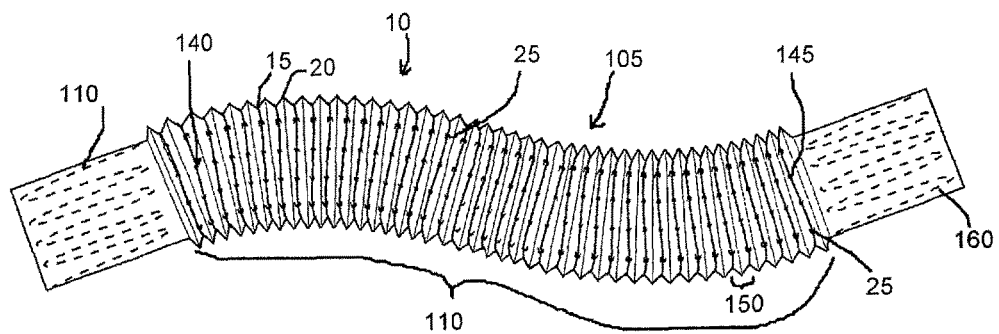
FIG. 4 shows the stent graft of FIG. 2 in another curved configuration.

Throughout the specification, the term "distal" means the end of an intraluminal device or part of the aorta that is further away from the heart in the direction of blood flow through the aorta. The term "proximal" means the end of an intraluminal device or part of the aorta that is nearer to the heart.

First Embodiment

FIG. 1 shows a first embodiment of a stent graft 100 in a deployed configuration in the descending thoracic aorta at the site of an aneurysm. The stent graft 100 includes a generally tubular body 105 formed of a biocompatible graft material. The generally tubular body 105 has a proximal end, a distal end and a slackened central portion 110. A lumen extends between the ends. The lumen of the tubular body 105 provides a path for blood to flow past the aneurysm and prevents blood from pressurizing the aneurysmal sac. The tubular body 105 formed of the graft material is supported by a framework of one or more stents. As shown in FIG. 1, the framework includes a first stent 115 having a sealing function at the proximal end of the generally tubular body 105, a second stent 135 having a flexing function in a central portion 110 of the generally tubular body 105, and a third stent 160 having a sealing function at the distal end of the generally tubular body 105.

Central Portion of Stent Graft

In the deployed configuration of the stent graft 100, the slackened central portion 110 has a non-taut or slackened configuration. For example, the central portion 110 may have a crimped or corrugated (accordion-like) configuration. Consequently, the tubular body 105 may change in length or curvature as needed to accommodate changes in the aorta. Typically, the tubular body 105 has an unextended length in the range of from about 100 mm to about 150 mm, with the capacity to lengthen an additional 5-100 mm. The additional possible length may be referred to as the "slackness" of the graft material.

The slackness also may be represented as a percentage of the unextended length. For example, the tubular body 105 may be configured to extend an amount corresponding to about 5%-100% of its unextended length. Deployed in the aorta with the graft material in a slackened state, the tubular body 105 is free to lengthen or contract. Generally, the tubular body 105 has an average diameter in the range of from about 22 to about 42 mm. For use in the iliac arteries, as shown for example in FIG. 25, the tubular body 105 of the stent graft 100 may have a diameter in the range of from about 10 mm to about 16 mm. In other portions of the vasculature, a suitable diameter may be in the range of from about 8 mm to about 36 mm. The diameter may be constant or variable along the length of the tubular body 105. Preferably, the graft material is substantially smooth and flat at both ends of the tubular body 105 to facilitate engaging with and sealing against the wall of the aorta upon deployment of the stent graft 100.

Extending along the slackened central portion 110 of the graft material and disposed distally adjacent to the first stent(s) 115, which will be discussed below, is the second stent 135, which can bend, lengthen and/or shorten along with the central portion 110. The second stent 135 is capable of expansion and contraction along a longitudinal axis thereof as well as motion off-axis (e.g., flexing or bending).

Preferably, the second stent 135 has a coiled configuration including a plurality of turns (e.g., helical turns) and thus may be referred to as a coiled stent 140. The coiled stent 140 may be formed of a wire having a gauge in the range of from about 0.7 mm to about 0.8 mm (0.014 in to about 0.021 in) that includes at least five helical turns (or coils) 145, with spacings 150 between the turns 145, as shown in FIG. 1A. The coiled stent 140 may include from 10 to 30 helical turns, according to one embodiment, and the stent also may include from 15 to 25 helical turns. Longer coiled stents 140 may include from 30 to 50 helical turns.

The spacing 150 between each turn 145 of the wire represents the pitch of the coiled stent. The pitch of the coiled stent may be constant or may vary over the length of the stent, depending on the configuration and positioning of the stent graft. Typical spacings are from about 1 mm to about 20 mm when deployed, from about 2 mm to about 10 mm, or from about 2 mm to about 5 mm. In another example, the spacings (or pitch) may be in the range of from about 5 mm to about 10 mm.

Referring to FIGS. 1 and 1A, the coiled stent 140 and the central portion 110 are configured to provide close apposition to the curvature of the vessel (e.g., the aorta) and to contract and expand longitudinally as needed. For example, shrinkage of an aortic aneurysm over time may modify the curvature of the aortic arch 170 and thereby cause a change in the length of the vessel. In order to allow the desired longitudinal and flexing motion of the coiled stent 140, the maximum deployed diameter d' of the helical turns 145 of the coiled stent 140 is preferably smaller than the minimum diameter of the vessel. The coiled stent 140 may be fixedly secured to the interior of the graft material at two locations at opposing ends of the stent by, for example, a monofilament or braided suture material 155. In addition, the coiled stent 140 may be slidingly secured to the graft material at additional locations along the central portion 110 between the ends of the stent 140. For example, portions of the coiled stent 140 may pass through loops of suture or graft material that are loose enough to permit the coils 145 of the stent 140 to slide through as needed. Alternatively, portions of the coiled stent 140 may be fixedly secured to the interior or exterior of the graft material throughout the central portion 110 by, for example, sutures 25, as shown in the exemplary stent graft 10 of FIG. 2. It is also envisioned that portions or substantially all of the coiled stent 140 may be fixedly secured to the graft material by an adhesive, as shown for example in FIGS. 14 and 15 and as further discussed below.

FIGS. 2-4 show the corrugated or crimped structure of the slackened central portion 110 of the tubular body 105 according to one embodiment. As shown in the figures, the central portion 110 may include helical crimps comprising alternate troughs 15 and crests 20 along the length thereof. The helical wire turns of the coiled stent 140 may be received in the troughs 15 of the helically crimped graft material. The wire turns may be retained in the troughs 15 by means of stitching with monofilament or braided sutures 25.

The helical reinforcement of the central portion 110 of the graft material with the coiled stent 140 is designed to prevent the tubular body 105 from closing off or kinking as it flexes to conform to the vasculature of the patient. The corrugations in the central portion 110 enable the tubular body to bend with one side becoming shorter and the other becoming longer to fit into the shape of a curve, as illustrated in FIGS. 2 and 4. On the shorter side, the corrugations move closer together and on the longer side, the corrugations move farther apart. The diameter of the central portion 110 preferably remains unchanged as the tubular body 105 flexes. The wire preferably terminates at each end of the central portion 110 in a loop 30, as shown in FIG. 3, which ensures that a pointed end of the wire cannot damage the vessel.

Figure 5:
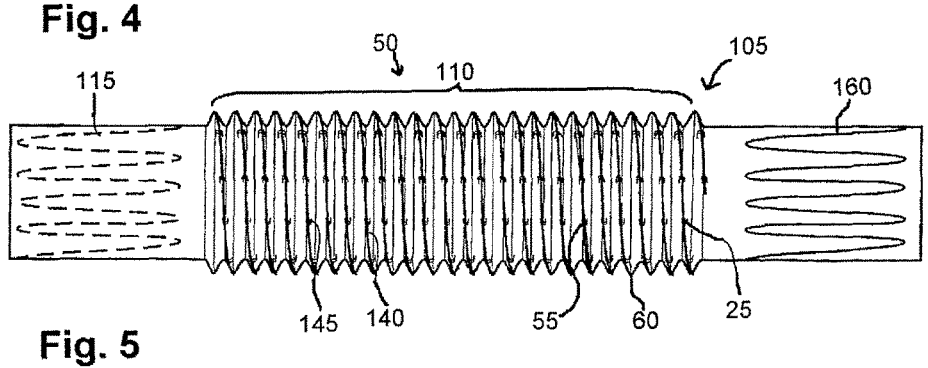
FIG. 5 shows a stent graft according to another alternative of the first embodiment.

FIG. 5 shows the corrugated or crimped structure of the central portion 110 of the tubular body 105 of an exemplary stent graft 50 according to another embodiment. In this figure, the central portion 110 includes a circumferential crimps (as opposed to a helical crimps, as in the previous embodiment) comprising alternate troughs 55 and crests 65 along the length thereof. The helical wire turns 145 of the coiled stent 140 are generally stitched on by means of sutures 25 and do not necessarily conform into the circumferential corrugations of the graft material. Still, supported by the coiled stent 140, the crimped graft material can maintain its diameter when flexing.

Figure 6A:
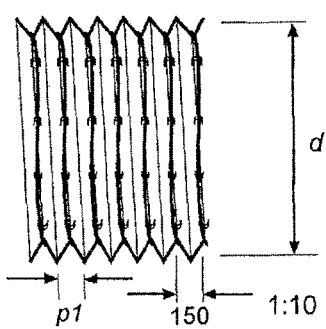
FIGS. 6A-6B and 7-8 are partial views of central portions of stent grafts according to several alternatives of the first embodiment.
Figure 6B:
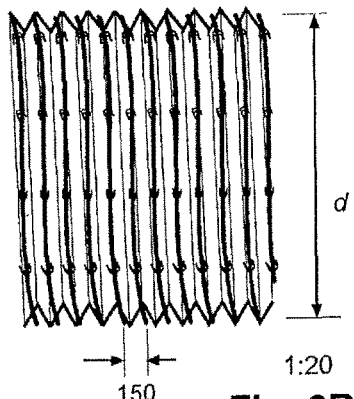

Referring to FIG. 6A, which shows a portion of the stent graft 100 of FIG. 1, the central portion 110 of the tubular body 105 may include a corrugated graft material of a diameter d with a crimp pitch $p_1$ and a helical wire pitch 150. The graft material is sized to fit closely over or within the coiled stent 140. Accordingly, the diameter d is substantially equal to the diameter d' of the coiled stent 140. In this embodiment, the crimp pitch $p_1$ and the helical wire pitch 150 are the same and are about one-tenth of the diameter d. Hence, a wire pitch 150 to diameter d ratio of about 1:10 is obtained for this configuration of the stent graft. In FIG. 6B, the wire pitch 150 to diameter d ratio is about 1:20.

Preferably, the coiled stent 140 includes at least two turns of wire 145 per length equivalent to the diameter d. In other words, the pitch to diameter ratio is no more than 1:1, or 1. For example, the helical wire pitch 150 to diameter d ratio may be in the range of from about 1:2 (0.5) to about 1:20 (0.05), or from about 1:5 (0.2) to about 1:10 (0.1). The diameter d of the tubular body 110 may be in the range of from, for example, about 6 mm to about 36 mm, and the helical pitch length (spacings between the turns) of the coiled stent 140 may be from, for example, about 2 mm to about 10 mm, as discussed above.

Figure 7:
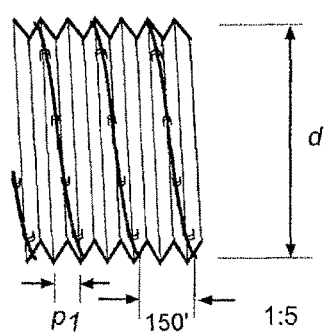

In FIG. 7, the pitch of the crimps $p_1$ is the same as shown in FIG. 6, and the pitch 150' of the helical wire is about twice that shown in FIG. 6; hence, the ratio of wire pitch 150' to diameter d of the tubular body is about 1:5.

Figure 8:
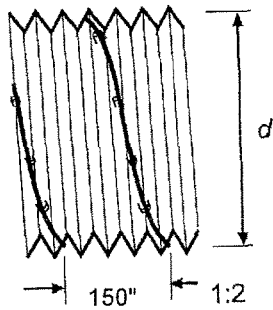

FIG. 8 shows a further embodiment in which the wire pitch 150" is about half of the diameter d of the tubular body, and thus the wire pitch to diameter d ratio is about 1:2.

Figure 9:
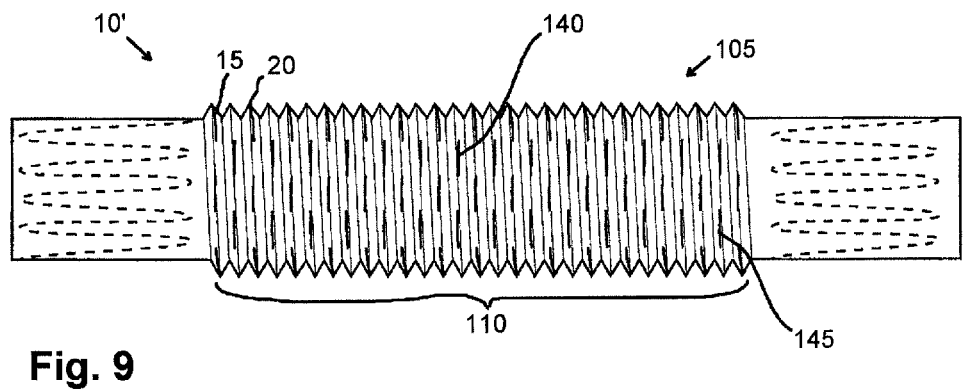
FIGS. 9-11 show stent grafts or partial views of stent grafts according to another alternative of the first embodiment.

The stent graft 10' of FIG. 9 includes a crimped or corrugated central portion 110 and a coiled stent 140 stitched thereto. In this embodiment, the helical turns 145 of the coiled stent 140 are stitched in and out of the helical or circumferential crimp of the central portion 110 to provide reinforcement for the stent graft 10'.

Figure 10:
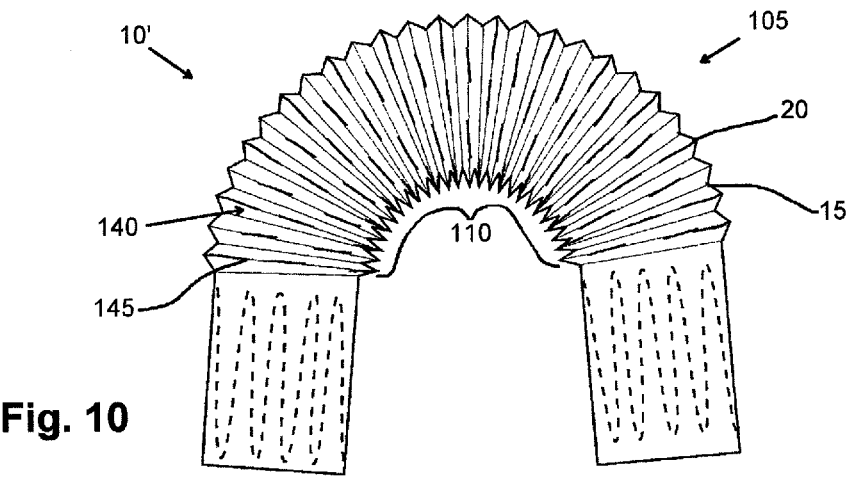
Figure 11:
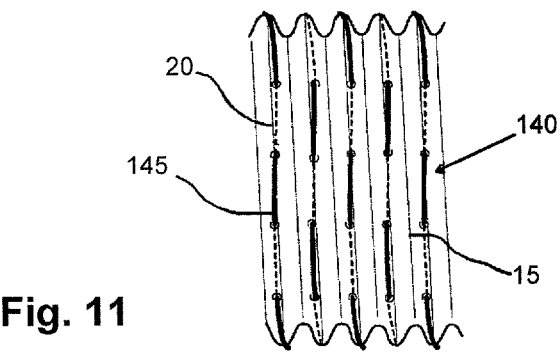

As with the stent graft 10 of FIG. 2, when the central portion 110 of the stent graft 10' shown in FIG. 9 is flexed, one side will shorten, and the other will lengthen to fit the vasculature without kinking or otherwise partially or fully closing off the tubular body 105. FIG. 10 shows the stent graft 10' in a curved configuration. FIG. 11 shows additional detail of a portion of the stent graft 10', and it can be seen that the helical turns 145 of the coiled stent 140 are stitched in and out of the crests 20 of the corrugations of the central portion 110. Alternatively, the helical turns of the coiled stent 140 could be stitched in through the troughs 15.

Figure 12:
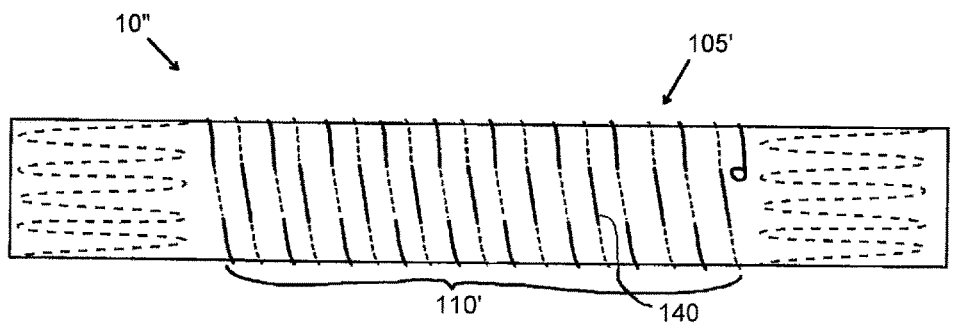
FIGS. 12 and 13 show stent grafts according to another alternative of the first embodiment.
Figure 13:
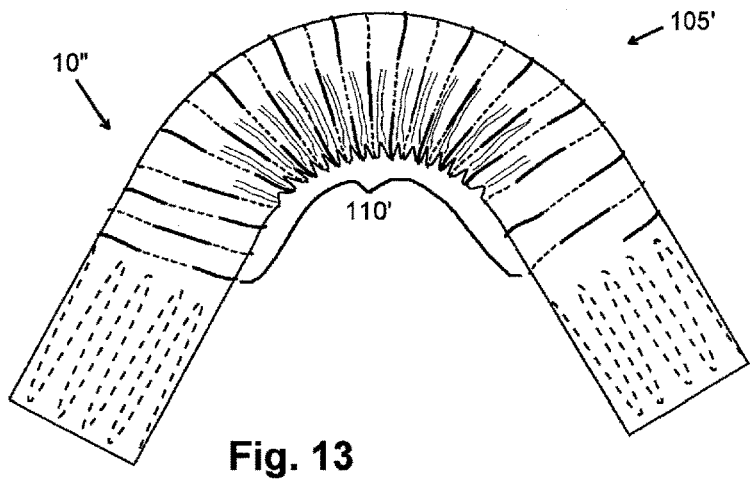

FIGS. 12 and 13 show a further embodiment of the stent graft 10" in which the central portion 110' does not have a corrugated structure and is continuous throughout the length of the tubular body 105'. A coiled stent 140 is shown stitched in and out of the graft material. When the stent graft 10" is bent, as shown in FIG. 13, the graft material at an outer radius of the bend cannot stretch any further, but the graft material at an inner radius of the bend can flex sufficiently to form a crimped arrangement without kinking or closing off the flow path through the tubular body 105'.

Figure 14:
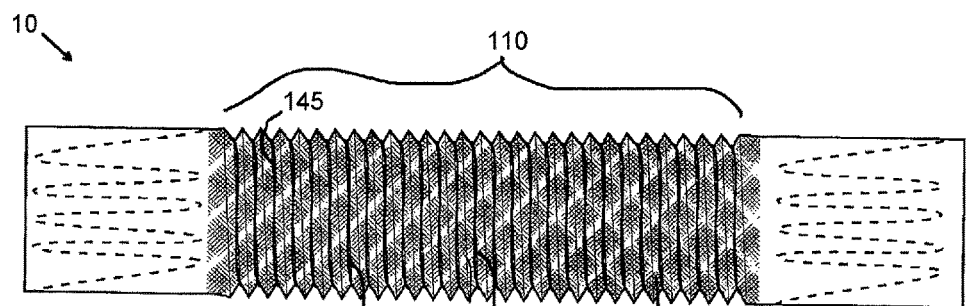
FIGS. 14 and 15 show stent grafts in which an adhesive is employed to adhere the stent to the graft material.
Figure 15:
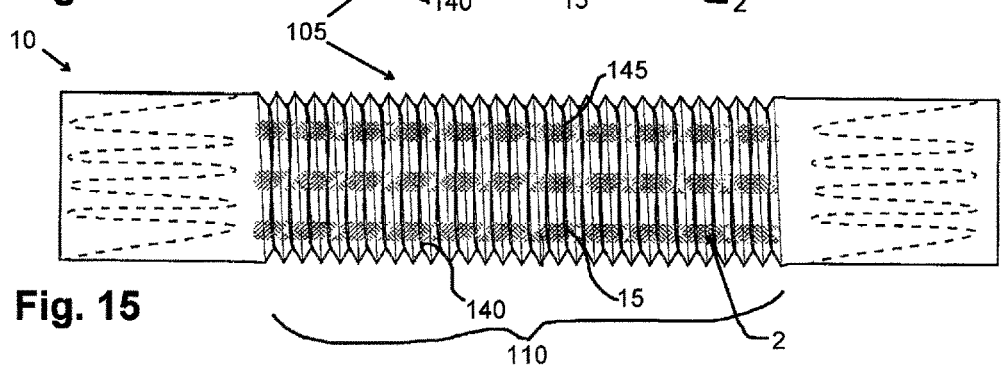

In FIG. 14, the helical turns 145 of the coiled stent 140 are retained within the troughs 15 of the corrugated central portion 110 of the stent graft 10 by means of a sprayed-on polymer adhesive 2. The polymer adhesive may be a urethane adhesive such as Thoralon™ sold by Cook Incorporated (Bloomington, Ind.). The adhesive may alternatively be painted on. In FIG. 15, the helical turns 145 of the coiled stent 140 are retained in the troughs 15 of the corrugated central portion 110 by means of longitudinal lines of adhesive 2. According to these embodiments, the turns 145 of the coiled stent 140 may be disposed within the troughs 15 of the central portion 110 on an outer side of the graft material, and the adhesive may be sprayed or painted on the tubular body 105 to hold the wire reinforcement in place. Alternatively, the coiled stent 140 may be adhered to an inner side of the graft material. The adhesive 2 may be applied over local regions of the central portion 110 (e.g., longitudinal or other directional strips) or over substantially all of the central portion 110.

Figure 16:
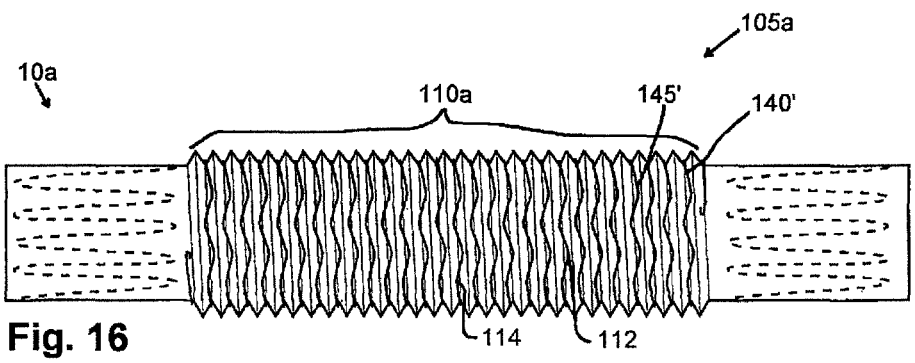
FIGS. 16-18 show stent grafts according to several alternatives of the first embodiment.

The coiled stent 140' of the stent graft 10a shown in FIG. 16 includes waves or crimps along the helical turns 145', thereby providing troughs 112 and crests 114 with approximately four to six troughs and crests per turn 145' of the wire. This arrangement may aid in compressing the central portion 110a of the stent graft 10a so as to enable it to be fitted into a deployment device.

Figure 17:
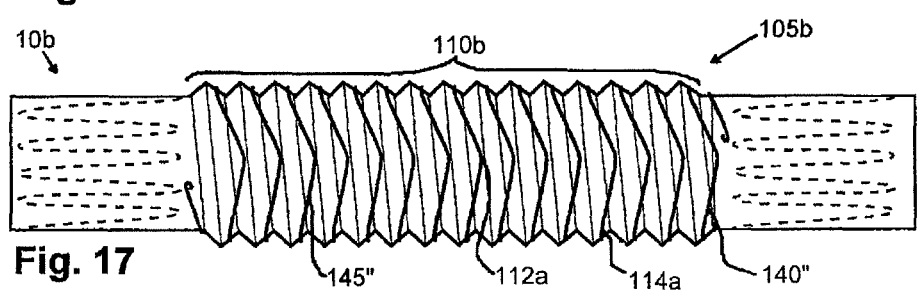

The stent graft 10b of FIG. 17 also has a portion in which the coiled stent 140" includes waves or crimps along the helical turns 145", thereby providing troughs 112a and crests 114a with two troughs and two crests per full turn of the coiled stent 140". In this embodiment, the central portion 110b of the graft material includes corrugations having a greater pitch than those shown in FIG. 16. The diameter of the tubular body 105b in this embodiment may be 12 mm and the central portion 110b may have a pitch of 4 mm. The helical wire pitch may also be 4 mm. Hence, the pitch to diameter ratio is 1:4. This arrangement may assist with compression of the stent graft 10b to enable it to be fitted into a deployment device.

Figure 18:
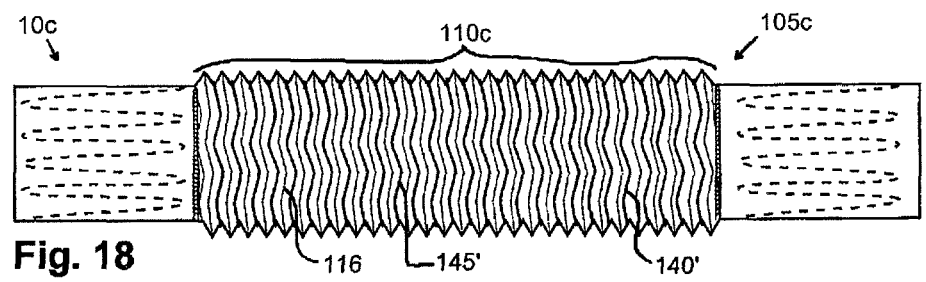

In the stent grafts 10a, 10b of FIGS. 16 and 17, the coiled stent 140', 140" is wavy or crimped as well as helical, and the crimping of the central portion 110c of the graft material is helical. In the stent graft 10c of FIG. 18, both the coiled stent 140' and the crimping of the graft material are wavy. The graft material is crimped to include a zigzag pattern 116 with crests and troughs along the helical crimps. This configuration is advantageous for disposing the helical turns 145' of the coiled stent 140' into the crimps of the tubular body 105c. Once the helical and crimped wire is laid into the wavy troughs of the graft material, an adhesive can be sprayed over it to retain it in place.

Figure 19:
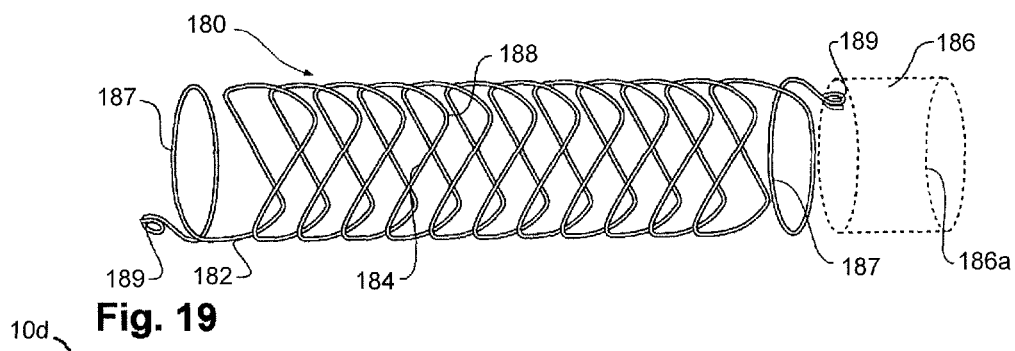
FIG. 19 shows an embodiment of a coiled stent.
Figure 20:
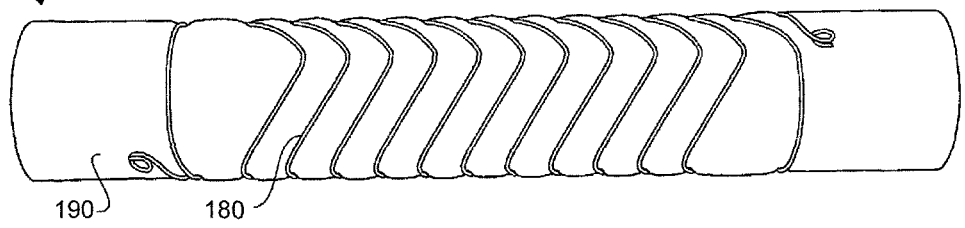
FIG. 20 shows a stent graft incorporating the coiled stent of FIG. 19.

FIG. 19 shows a further embodiment of a coiled or spiral stent for a stent graft and FIG. 20 shows a stent graft 10d incorporating the stent 180 of FIG. 19.

The stent 180 of FIG. 19 comprises a continuous helix of resilient wire 182 such as Nitinol. The wire is heat set into the shape shown by known techniques. The helical shape defines a cylindrical surface 186 as indicated by the cylindrical surface designated by the dotted lines 186a. Each turn of the helix is formed into a series of waves or zig zag shapes with the waves 184 being formed to lie on the cylindrical surface 186. In this embodiment, there are four bends 188 for each turn but there may be from two to eight bends per turn. The wavy spiral at each end preferably terminates in a non-wavy spiral turn 187 at each end of the stent. As in the earlier embodiments, the helical wire pitch to diameter ratio can be from 1:2 to 1:20. Preferably it is in the range of 1:5 to 1:10. The wire 182 terminates at each end in a loop 189 which ensures that a pointed end of the wire cannot damage the vasculature into which it is placed. An advantage of the wavy helical shape of the stent 180 is that it combines the high flexibility of the helical stent as shown in the earlier embodiments with the ease of compression of a zig-zag Gianturco style stent which facilitates loading into a delivery device.

FIG. 20 shows the stent 180 of FIG. 19 mounted onto a tubular similarly crimped biocompatible graft material 190 such as Dacron™ to form a stent graft 10d. The graft material is similarly crimped by being placed onto a shaped former and restrained in the crimped shape while being heat set. In this embodiment, the stent is retained onto the graft material by being adhered thereto by a biocompatible adhesive material, such as Thoralon™.

Proximal and Distal Ends of Stent Graft

Referring again to FIG. 1, a first stent 115 that performs a sealing function may be provided at the proximal end of the tubular body 105. The first stent is preferably a zigzag stent 120 that includes a series of bends 125 with struts 130 between the bends. Preferably, the struts 130 have a length in the range of from about 3 mm to about 20 mm, and more preferably from about 5 mm to about 15 mm, which is reduced compared to the length of the struts forming conventional zigzag stents. If the length is too long, a gap may develop between the struts 130 and the aortic wall in a region of high curvature, and the seal provided by the stent 120 may be compromised. Accordingly, the length is preferably sufficiently short that the struts 130 may substantially conform to the curved aortic wall, but also long enough that they may exert a sufficient outward radial force to provide the desired sealing function. It may be advantageous for the struts 130 to be asymmetric in length about the circumference of the zigzag stent 120 to better conform to the curvature of the aortic arch, as described in U.S. patent application Ser. No. 11/975,950, which was filed on Oct. 23, 2007, and is hereby incorporated by reference. For example, struts 130 positioned on the underside of the arch, where the curvature is higher, may have a shorter length than struts 130 situated over the arch, where the curvature is somewhat reduced. For example, the struts 130 along the underside of the arch may be about 5 mm or less in length, while the struts 130 passing over the arch may have a length of about 10-15 mm, for example. Alternatively, as shown in FIG. 2, a zigzag stent 120' having a conventional strut length may be employed as the first stent 115. Such a stent may be suitable for applications in the iliac arteries, for example, as will be discussed further below.

The first stent 115 preferably has a maximum deployed diameter that is oversized by about 10% to 20% with respect to the native aorta diameter so as to provide the desired outward pressure on the vessel wall. The oversizing is typically about 15-20% in the case of an aneurysm and about 10-15% in the case of a dissection.

Two or more first stents 115 (e.g., zigzag stents 120) may be disposed at the proximal end of the tubular body 105 to improve the sealing capability of the stent graft 100. The sealing capability and migration resistance of the device may be further enhanced by employing barbs configured to penetrate and grasp tissue. The barbs may be attached to or integrally formed with the first stent(s) 115.

The first stent(s) 115 are preferably secured to the interior of the graft material by using, for example, a monofilament or braided suture material. Sutures 155 may be used at multiple locations along the stent 115, 120 and about the circumference of the tubular structure 105 to secure the first stent 115 to the graft material.

Referring again to FIG. 1, one or more third stents 160 that perform a sealing function are preferably disposed adjacent to the second stent 135 (coiled stent 140) at the distal end of the stent graft 100. The third stent 160 may be a zigzag stent 165 that is oversized in diameter compared to the native diameter of the aorta and has struts of a typical length (e.g., from about 21 mm to about 22 mm). The third stent 160 is preferably secured to the interior of the graft material.

Second Embodiment

FIG. 21 shows, according to a second embodiment, a stent graft 200 in a deployed configuration in the descending thoracic aorta at the site of an aneurysm. The stent graft 200 includes a generally tubular body 205 formed of a graft material and having a proximal end, a distal end, and a slackened central portion 210. A lumen extends between the ends. The lumen of the tubular body 205 provides a path for blood to flow past the aneurysm and prevents blood from pressurizing the aneurysmal sac. The tubular body 205 formed of the graft material is supported by a framework of one or more stents. As shown in FIG. 21, the framework includes a coiled stent 115 having both a sealing function and a flexing function that extends from the proximal end of the generally tubular body 105 into the central portion 210. The framework also includes at least one sealing stent 260 disposed adjacent to the coiled stent 215 at the distal end of the stent graft 200. The central portion 210 of the stent graft 200 of this embodiment may include any or all of the features described previously.

According to the second embodiment, the coiled stent 215 has a sealing portion 220 and a flexing portion 225 and extends from the proximal end of the tubular body 205 along the central portion 210. The sealing portion 220 of the coiled stent 215 includes at least one helical turn (or coil) and may be formed of a wire having a gauge in the range of from about 0.8 mm to about 1 mm (about 0.021 inch to about 0.025 in). Preferably, the sealing portion 220 includes at least two complete helical turns 230.

As shown in FIG. 21A, the turns 230 of the sealing portion 220 may include a small spacing 235 the turns, such as from about 0.1 mm to about 1 mm. Preferably, the spacing 235 between the turns 230 of the sealing portion 220 is about 0.5 mm or less. For example, the sealing portion 220 of the coiled stent 215 may be contracted to its minimum length such that the turns include substantially no spacing (i.e., adjacent coils are in direct contact). The sealing portion 220 of the coiled stent 215 preferably has a maximum deployed diameter $d_2$ that is oversized by about 10% to about 20% with respect to the native diameter of the aorta so as to provide the desired outward pressure on the aortic wall from the closely spaced coils 230. The oversizing is typically about 15-20% in the case of an aneurysm and about 10-15% in the case of a dissection.

The sealing capability and migration resistance of the stent graft 200 may be further enhanced by employing barbs configured to penetrate and grasp tissue. The barbs may be attached to or integrally formed with the sealing portion 220 of the coiled stent 215.

Preferably, the sealing portion 220 of the coiled stent 215 is secured to the interior of the graft material using, for example, a monofilament or braided suture material. Sutures 240 may be used at multiple locations along the sealing portion 220 of the stent 215 and about the circumference of the tubular structure 205 to secure the sealing portion 220 of the stent 215 to the graft material. Alternatively, the sealing portion 220 may be fixedly secured to the exterior of the graft material by, for example, sutures or an adhesive.

The flexing portion 225 of the coiled stent 215 can bend, lengthen and/or shorten along with the central portion 210. The flexing portion 225 is capable of expansion and contraction along a longitudinal axis thereof as well as motion off-axis (e.g., flexing). Preferably, the flexing portion 225 has a coiled configuration including a plurality of turns (e.g., helical turns). The flexing portion 225 may be integrally formed with the sealing portion 220 of the coiled stent 215, or it may be fabricated separately and attached to the sealing portion 220 by welding, bonding or another attachment method. Hence, like the sealing portion 220, the flexing portion 225 of the coiled stent 215 may be formed from a wire having a gauge in the range of from about 0.8 mm to about 1.0 mm, or the flexing portion 225 may be formed from a wire having a smaller gauge (e.g. from about 0.7 mm to about 0.8 mm) for enhanced flexibility of the central portion 210 of the stent graft 200.

As shown in FIGS. 21 and 21B, the flexing portion 225 of the coiled stent 215 preferably includes at least five helical turns 245 with spacings 250 between the turns 245. For example, the flexing portion 225 may include from 10 to 30 helical turns. The flexing portion 225 also may include from 15 to 25 helical turns. Longer coiled stents 215 may include from 30 to 50 helical turns.

The spacing 250 between each turn 245 of the wire represents the pitch of the flexing portion 225 of the coiled stent 215. The spacings between the helical turns may be constant or may vary over the length of the coiled stent 215, depending on the configuration and positioning of the stent graft 200. Typical spacings are from about 1 mm to about 20 mm when deployed. For example, the spacings (or pitch) may be in the range of from about 2 mm to about 10 mm, or from 5 mm to about 10 mm.

Similar to the coiled stent 140 of the previous embodiment, the flexing portion 225 of the coiled stent 215 may have a diameter which is substantially the same as that of the tubular body 205 formed of the graft material so that the graft material fits closely over or within the flexing portion 225. Preferably, the flexing portion 225 includes at least two turns of wire per length equivalent to the diameter. In other words, the pitch to diameter ratio is no more than 1:1, or 1. For example, the helical wire pitch 150 to diameter d ratio may be in the range of from about 1:2 (0.5) to about 1:20 (0.05), or from about 1:5 (0.2) to about 1:10 (0.1).

The flexing portion 225 of the coiled stent 215 is configured to provide close apposition to the curvature of the vessel (e.g., the aorta) and to contract and expand longitudinally as needed. For example, shrinkage of an aortic aneurysm over time may modify the curvature of the aortic arch and cause a change in the length of the vessel. In order to provide the desired longitudinal and flexing motion of the coiled stent 215, the maximum expanded diameter $d_3$ of the helical turns 230 of the flexing portion 225 is preferably smaller than the native diameter of the aorta.

Opposing ends of the flexing portion 225 of the coiled stent 215 are preferably fixedly secured to the interior of the graft material by, for example, a monofilament or braided suture material. In addition, the flexing portion 225 of the coiled stent 215 may be slidingly secured to the graft material at additional locations between the ends of the flexing portion 225. For example, portions of the coiled stent 215 may pass through loops of suture or graft material 255 that is loose enough to permit the coils of the stent 215 to slide through as needed. Alternatively, regions of the flexing portion 225 of the coiled stent 215 may be fixedly secured to the interior or exterior of the graft material throughout the central portion 110 by, for example, sutures or an adhesive.

Referring again to FIG. 21, at least one stent 260 that performs a sealing function is preferably disposed adjacent to the flexing portion 225 of the coiled stent 215 at the distal end of the stent graft 200. The sealing stent 260 may be a zigzag stent 265 that is oversized in diameter compared to the diameter of the aorta and has struts of a typical length (e.g., from about 21 mm to about 22 mm). The sealing stent 260 is preferably secured to the interior of the graft material.

Third Embodiment

Figure 22A:
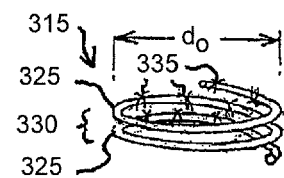
FIGS. 22A-22B show close-up views of portions of the stent graft of FIG. 22.
Figure 22:
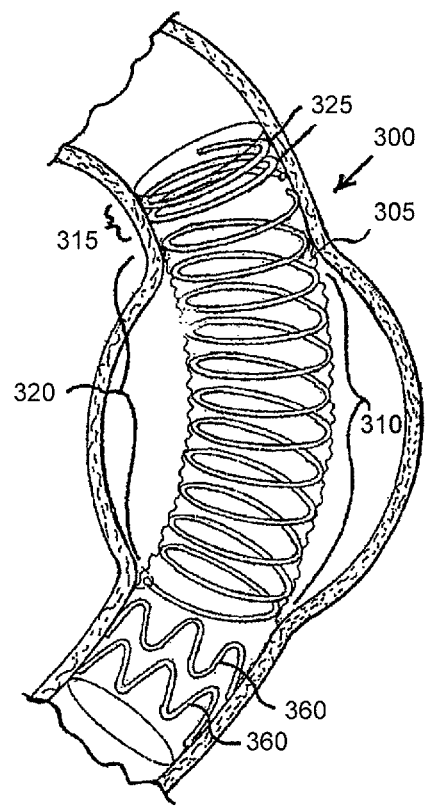
FIG. 22 shows a stent graft according to a third embodiment in a deployed configuration in the descending thoracic aorta.

FIG. 22 shows, according to a third embodiment, a stent graft 300 in a deployed configuration in the descending thoracic aorta at the site of an aneurysm. The stent graft 300 includes a generally tubular body 305 formed of a graft material and having a proximal end, a distal end, and a slackened central portion 310. A lumen extends between the proximal and distal ends. The lumen of the tubular body 305 provides a path for blood to flow past the aneurysm and prevents blood from pressurizing the aneurysmal sac. The tubular body 305 is supported by a framework of one or more stents.

As shown in FIG. 22, the framework includes a first coiled stent 325 having a sealing function at the proximal end of the tubular body 305 and a second coiled stent 320 having a flexing/lengthening function adjacent to the first coiled stent 325. The second coiled stent 320 extends along the central portion 310 of the stent graft 300. The central portion 310 of the stent graft 300 of this embodiment may include any or all of the features described previously. A third stent 360 having a sealing function is disposed at the distal end of the tubular body 305.

As shown in FIG. 22A, the first coiled stent 315 may be formed of a wire having a gauge in the range of from about 0.8 mm to about 1.0 mm and may include at least one complete helical turn (or coil). Preferably, the first coiled stent 315 includes at least two complete helical turns 325. The turns 325 of the first coiled stent 315 may include a small spacing 330 between the turns, such as from about 0.1 mm to about 1 mm. Preferably, the spacing 330 between the turns 325 is about 0.5 mm or less. For example, the first coiled stent 315 may be contracted to its minimum length such that the coils 325 include no spacing between them.

The first coiled stent 315 preferably has a maximum deployed diameter $d_0$ that is oversized by about 10% to about 20% with respect to the native diameter of the aorta so as to provide the desired outward force on the aortic wall from the closely spaced coils 325. The oversizing is typically about 15-20% in the case of an aneurysm and about 10-15% in the case of a dissection.

The sealing capability and migration resistance of the stent graft 300 may be further enhanced by employing barbs configured to penetrate and grasp tissue. The barbs may be attached to or integrally formed with the first coiled stent 315.

The first coiled stent 315 may be secured to the interior or exterior of the graft material using, for example, a monofilament or braided suture material. Sutures 335 may be used at multiple locations along the first coiled stent 315 and about the circumference of the tubular structure 305 to secure the stent 315 to the graft material.

The second coiled stent 320 imparts a flexing and lengthening capability to the stent graft 300, as shown in FIG. 22. The second coiled stent 320 is capable of expansion and contraction along a longitudinal axis thereof as well as motion off-axis (e.g., flexing). Preferably, the second coiled stent 320 has a coiled configuration including a plurality of turns (e.g., helical turns). Like the first coiled stent 315, the second coiled stent 320 may be formed from a wire having a gauge in the range of from about 0.8 mm to about 1.0 mm. Preferably, the second coiled stent 320 is formed from a wire having a smaller gauge (e.g. from about 0.7 mm to about 0.8 mm) so as to enhance the flexibility of the central portion 310 of the stent graft 300.

Figure 22B:
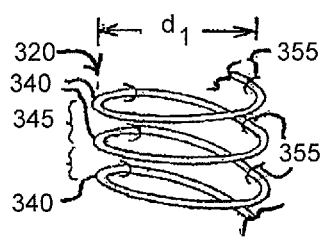

As shown in FIGS. 22 and 22B, the second coiled stent 320 preferably includes at least five helical turns 340 with spacings 345 between the helical turns 340. For example, the second coiled stent 320 may include from 10 helical turns to 30 helical turns with spacings between the turns, or from 15 helical turns to 25 helical turns with spacings between the turns. The spacings 345 between the helical turns may be constant or may vary over the length of the second coiled stent 320. Typical spacings 345 are from about 1 mm to about 20 mm when deployed. For example, the spacings 345 may be in the range of from about 2 mm to about 10 mm, of from about 5 mm to about 10 mm.

Similar to the coiled stent 140 of the first embodiment, the second coiled stent 320 may have a diameter which is substantially the same as that of the tubular body 305 formed of the graft material so that the graft material fits closely over or within the second coiled stent 320. Preferably, the second coiled stent 320 includes at least two turns of wire per length equivalent to the diameter. In other words, the pitch to diameter ratio is no more than 1:1, or 1. For example, the helical wire pitch 150 to diameter d ratio may be in the range of from about 1:2 (0.5) to about 1:20 (0.05), or from about 1:5 (0.2) to about 1:10 (0.1).

The second coiled stent 320 is configured to provide close apposition to the curvature of the aorta and to contract and expand longitudinally as needed. For example, shrinkage of an aortic aneurysm over time may modify the curvature of the aortic arch and cause a change in the length of the vessel. To accommodate such changes, the second coiled stent 320 is preferably free to move longitudinally within the aorta. Accordingly, the maximum deployed diameter $d_1$ of the helical turns of the second coiled stent 320 is preferably smaller than the native diameter of the aorta. The second coiled stent 320 is preferably fixedly secured to the interior of the graft material at two locations at opposing ends of the stent 320 by a monofilament or braided suture material, for example. In addition, the second coiled stent 320 may be slidingly secured to the graft material at additional locations between the ends of the stent 320. For example, portions of the second coiled stent 320 may pass through loops of suture or graft material 355 that is loose enough to permit the coils 340 of the stent 320 to pass through as needed. Alternatively, portions of the second coiled stent 320 may be fixedly secured to the interior or exterior of the graft material throughout the central portion 110 by, for example, sutures or an adhesive.

Referring again to FIG. 22, at least one third stent 360 that performs a sealing function is preferably disposed adjacent to the second coiled stent 320 at the distal end of the stent graft 300. The third stent 360 may be a zigzag stent that is oversized in diameter compared to the diameter of the aorta so as to provide an outward radial force on the aortic wall. The third stent 360 may have struts of a typical length (e.g., from about 21 mm to about 22 mm). The third stent 360 is preferably secured to the interior of the graft material.

Materials

The graft material may comprise a woven or nonwoven sheet that is rolled to form the tubular body described herein, according to one embodiment. The graft material is typically pulled over the stent(s) and secured to structural components of the stent(s) by sutures or by loops of graft material. Many different types of natural or synthetic graft materials may be employed to form the tubular body of the stent graft. Preferably, the graft material is biocompatible. For example, the graft material may be formed in whole or in part from one or more polyesters, such as poly(ethylene terephthalate) or Dacron®; fluorinated polymers, such as polytetrafluoroethylene (PTFE) and expanded PTFE; polyurethanes; polypropylene; polyaramids; polyacrylonitrile; nylons; small intestinal submucosa (SIS); and/or cellulose. SIS may be advantageous in some cases because the material includes growth factors that encourage cell migration within the graft material, which eventually results in replacement of the graft material with organized tissues. Graft materials that are not inherently biocompatible may be suitable for use in the stent graft if they can be rendered biocompatible by, for example, surface modification techniques. Examples of surface modification techniques include graft polymerization of biocompatible polymers from the material surface, coating of the surface with a crosslinked biocompatible polymer, chemical modification with biocompatible functional groups, and immobilization of a compatibilizing agent, such as heparin or other substances. It is also envisioned that the graft material may be impregnated or coated with one or more therapeutic drugs for release at the site of the aneurysm.

The stents supporting the tubular body are preferably made from a biocompatible metal or metal alloy, such as stainless steel, nickel-titanium (e.g., Nitinol), gold, platinum, palladium, titanium, tantalum, tungsten, molybdenum, or alloys thereof. Other suitable alloys for the stents include cobalt-chromium alloys such as L-605, MP35N, and Elgiloy; nickel-chromium alloys, such as alloy 625; and niobium alloys, such as Nb-1% Zr, and others. Preferably, the material is MRI-compatible and does not produce artifacts in images or scans obtained from magnetic resonance imaging. The stents may be fabricated from wire, tubing, or sheet using metal working and finishing techniques known in the art, such as drawing, extrusion, cold forming, gun drilling, laser welding, and laser cutting technologies. One or more of the stents of the stent graft may alternatively be made from a non-metallic material, such as a thermoplastic or other polymer. The stents may be designed to be either balloon-expandable or self-expanding.

According to an embodiment in which one or more of the stent(s) are self-expanding, the material of the self-expanding stent preferably has shape memory/superelastic characteristics that enable it to "remember" and recover a previous shape. In the case of nickel-titanium shape memory alloys, the source of the shape recovery is a phase transformation between a lower temperature phase (martensite) and a higher temperature phase (austenite), which may be driven by a change in temperature (shape memory effect) or by the removal of an applied stress (superelastic effect). Strain introduced into the alloy in the martensitic phase to achieve a shape change may be substantially recovered upon completion of a reverse phase transformation to austenite, allowing the alloy to return to the previous shape. Recoverable strains of up to about 8-10% are generally achievable with nickel-titanium shape memory alloys. Other suitable shape memory alloys for the stent may include, for example, Cu—Zn—Al alloys and Fe—Ni—Al alloys.

Delivery, Deployment and Use

The stent graft described herein according to various embodiments has, or is collapsible into, a low-profile, reduced diameter configuration suitable for loading into an intraluminal delivery system. Typical delivery systems may range in size from 18 Fr to 24 Fr. The stents may be fabricated in a low-profile configuration suitable for delivery and then expanded to a larger diameter only after being deployed in the aorta, or they may be deformed into the desired collapsed state after fabrication and processing at the desired deployment diameter. For example, nickel-titanium self-expanding stents typically undergo a heat-setting treatment at the deployment diameter during fabrication, and thus are generally deformed into a reduced diameter configuration for delivery into the body.

Figure 23A:
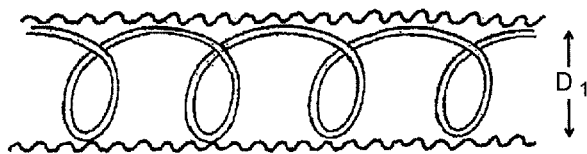
FIGS. 23A-23C show schematically an embodiment of a central portion of a stent graft in an exemplary deployed configuration (FIG. 23A) of diameter $D_1$ and in two exemplary delivery configurations (FIGS. 23B and 23C) of diameter $D_2$.
Figure 23B:
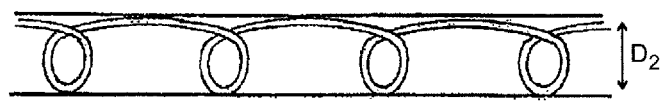
Figure 23C:

In the case of the exemplary zigzag stents described herein, the low-profile configuration may be attained when the included angle of the bends between adjacent struts is minimized. In the case of the exemplary coiled stents described herein, the low-profile configuration may be attained when the stent is lengthened relative to the deployed state such that the coil diameter $D_1$ is reduced to a smaller diameter $D_2$, as shown schematically in FIGS. 23A and 23B. Alternatively, the low-profile configuration may be attained by forming the stent into a coiled shape that has a similar length as the deployed configuration but an increased number of smaller diameter coils, as shown schematically in FIGS. 23A and 23C. Because at least a portion of the graft material is fabricated to have an accordion-like or other slackened (non-taut) configuration when deployed, and because the coiled stent may be slidably attached to the graft fabric by sutures or fabric loops, the tubular structure of the graft is able to accommodate a different arrangement of the coils or stent length for delivery. In addition, the embodiments shown in FIGS. 16-20 and described above may facilitate compressing the stent graft to a reduced diameter configuration for insertion into a delivery system.

Figure 24:
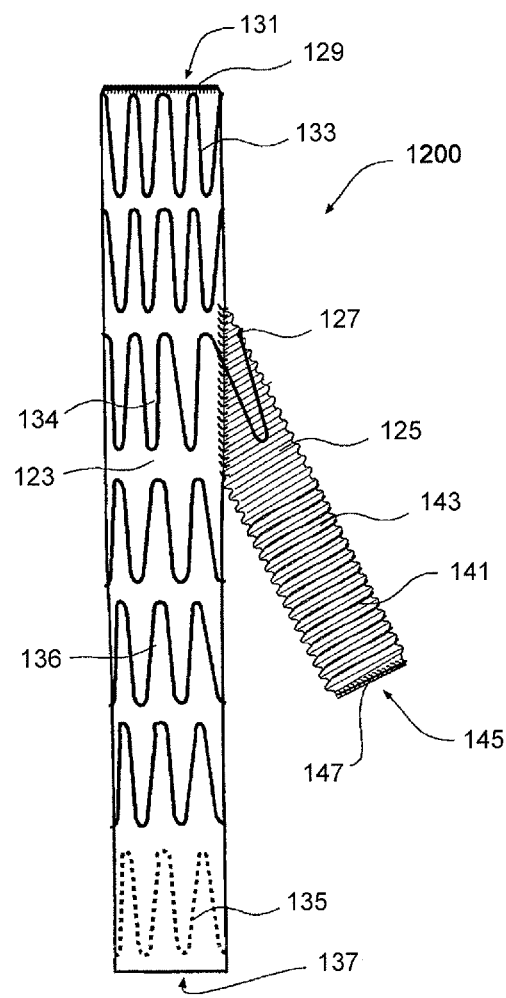
FIG. 24 shows one embodiment of the stent graft in use in the vasculature of a patient.

FIG. 24 shows the use of a coiled stent of the present disclosure for a side arm of a stent graft, such as an iliac artery stent graft. The stent graft 1200 comprises a tubular body 123 with a side arm 125, which is also a tubular body, stitched into an aperture in the main body 123 at juncture 127 so as to allow fluid communication from the lumen of the main body into the lumen of the side arm 125. The main tubular body 123 has a reinforcing ring arrangement 129 at its proximal end 131. The tubular body 123 also has a number of external zigzag self-expanding stents 133, 134 and 136 along its length and an internal self-expanding zigzag stent 135 at its distal end 137.

Patent Cooperation Treaty patent application no. PCT/US2005/033676, entitled "Side Branch Stent Graft," includes discussion of one method of connection of a side arm to a main tubular body in a stent graft, and the disclosure of this patent specification is hereby incorporated by reference in its entirety.

Patent Cooperation Treaty patent application no. PCT/US2006/021258 (WO/2006/130755), entitled "Side Branch Stent Graft," includes discussion of various configurations of iliac artery stent grafts with a side arm, and the disclosure of this patent specification is hereby incorporated by reference in its entirety.

The side arm 125 includes a helically or circumferentially crimped biocompatible graft material body and a portion 141 having a coiled stent 143 affixed to the graft material. The construction of this portion may be as depicted in any of the preceding figures. At the distal end 145 of the side arm portion 141 there is a reinforcing ring 147 to provide a fixed size of aperture at the end of the side arm so as to allow expansion of a balloon inflatable or self expanding stent therewithin to enable sealing at the aperture.

The main tubular body 123 of the stent graft 1200 depicted in FIG. 24 may have a diameter of from about 12 mm to about 16 mm. The side arm of the stent graft 1200 may have a diameter of from about 6 mm to about 8 mm. The side arm may have a length of from about 12 mm to about 40 mm.

Figure 25:
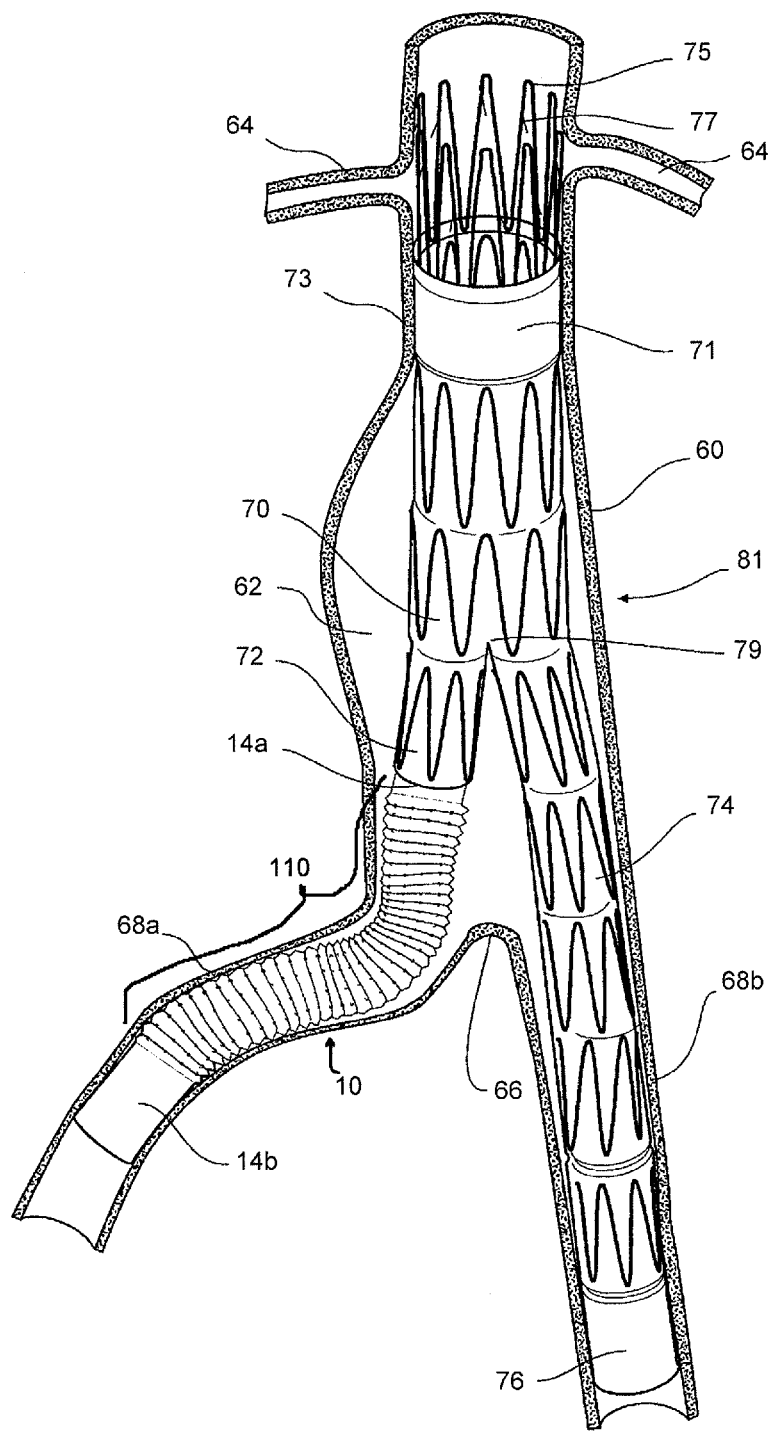
FIG. 25 shows another embodiment of the stent graft in use in the vasculature of a patient.

FIG. 25 shows the use of a stent graft of the present disclosure in a vasculature of a patient, in particular, in the aorta and aortic bifurcation extending down towards the iliac arteries. The vasculature comprises an aorta 60 in the region between the renal arteries 64 and the aortic bifurcation 66. Common iliac arteries 68a and 68b extend from the aortic bifurcation 66. The common iliac artery 68a has a considerable kink in it. The aorta 60 has an aneurysm 62 which extends between the renal arteries and the iliac bifurcation.

To traverse the aneurysm, a bifurcated aortic stent graft 40 has been deployed into the aorta 60. The proximal end 71 of the bifurcated stent graft 70 is engaged onto a non-aneurysed portion 73 of the aorta just distal of the renal arteries 64. To ensure good fixation, the stent graft 70 includes a supra renal exposed stent 75 with barbs 77 engaging the wall of the aorta proximal of the renal arteries 64.

The stent graft 70 has a short leg 72 and a long leg 74 extending from a bifurcation 79 at its distal end 81. The long leg 74 has a sealing surface 76 at its distal end, and this engages in a sealing manner into a non-aneurysed portion of the common iliac artery 68b.

A leg extension stent graft ("leg extension") 10 of the type shown in FIG. 2 has been deployed into the iliac artery 68a. The sealing surface 14 at the proximal end 14a of the leg extension 10 lies within the shorter leg 72 of the bifurcated stent graft 70, and the leg extension 10 extends down into the iliac artery 68a. The reinforced crimped central portion 110 of the leg extension 10 allows for a degree of convolution in the iliac artery 68a while still allowing the sealing surface 14 at the distal end 14b of the leg extension 10 to seal conveniently within the iliac artery 68a.

Figure 26:
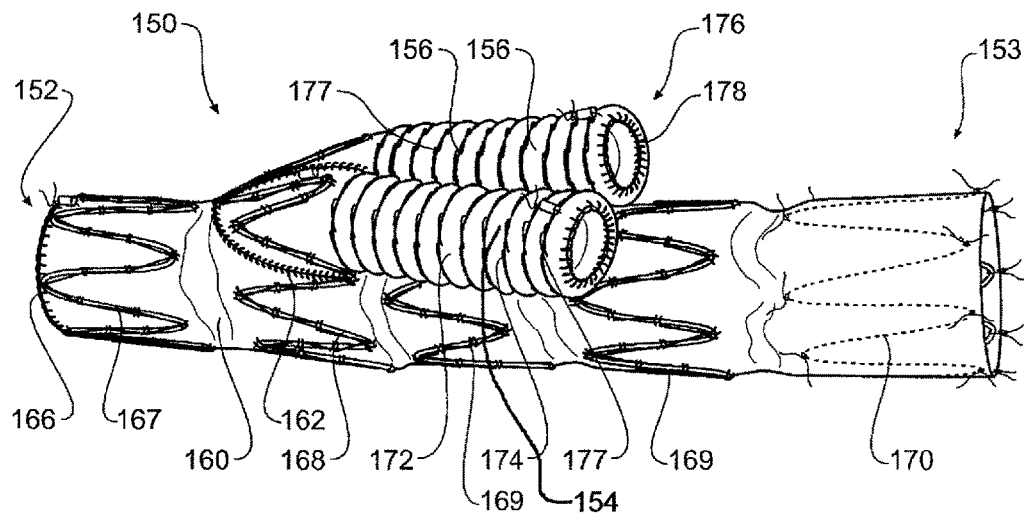
FIG. 26 shows an alternative embodiment of the stent graft incorporating twin highly flexible stent graft side branches.
Figure 27:
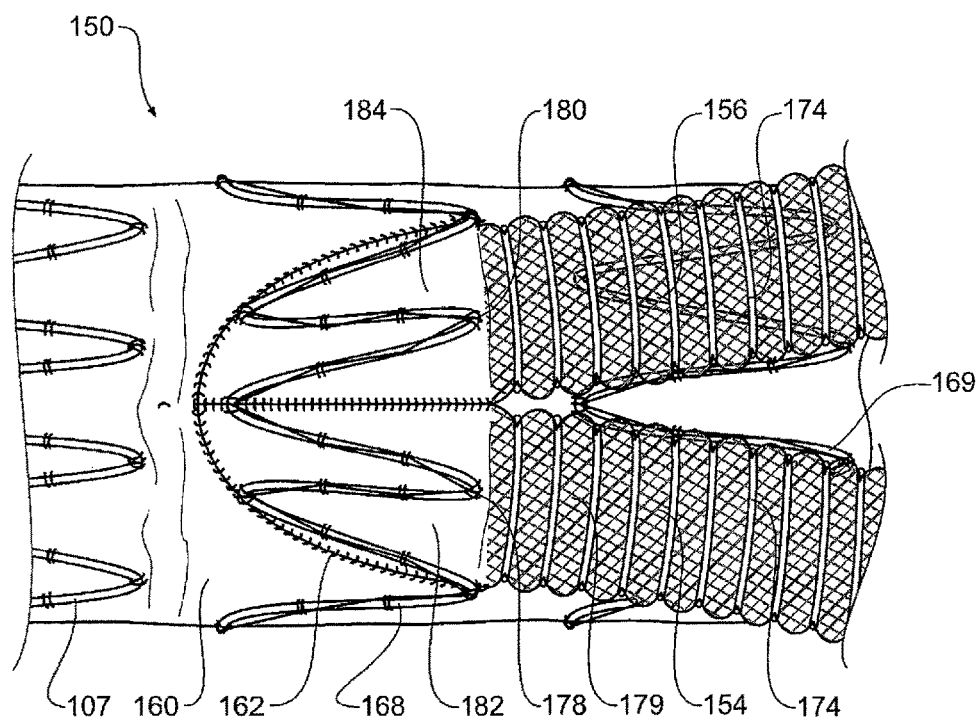
FIG. 27 shows a detailed elevation view of the embodiment shown in FIG. 26.

FIG. 26 shows an alternative embodiment of a stent graft incorporating twin highly flexible stent graft side branches. FIG. 27 shows a detailed elevation view of the embodiment shown in FIG. 26 but with a different form of affixing of the reinforcing wire to the stent graft material.

In FIGS. 26 and 27, a stent graft 150 with twin side branches is depicted. This device is intended for use in the iliac artery region of a patient where the proximal end 152 is intended to connect with a bifurcated aortic or aorto-uni-iliac stent graft device, the distal end 153 is intended to extend down the external iliac artery either directly or with a iliac leg extension (not shown), one side arm 154 is intended to have a leg extension deployed thereinto to extend into an internal iliac artery and the other side arm 156 is intended to have a leg extension deployed thereinto to extend into any other vessel in the region. Such a requirement may exist where the superior gluteal artery, for instance, which extends from the internal iliac artery has an origin which is close to the origin of the internal iliac artery or the aneurysm, for which the iliac artery stent graft is being used, extends into the internal artery. A leg extension can be a covered or uncovered stent.

In FIGS. 26 and 27 it may be seen that a stent graft 150 comprises a tubular body 160 with side arms 154 and 156, each also a tubular body, stitched into an aperture in the main body 160 at 162 so as to allow fluid communication from the lumen of the main body into the lumens of the side arms. The main tubular body 160 has a reinforcing ring arrangement 166 at its proximal end 152. The tubular body 160 also has a number of external zig-zag self-expanding stents 167, 168 and 169 along its length and an internal self-expanding zig-zag stent 170 at its distal end 153.

On each of the side arm arms 154 and 156 there is a portion 172 which has a helically or circumferentially crimped biocompatible graft material body and a helical reinforcing wire (or coiled stent) 174 affixed to the graft material. The construction of this portion may be any of those the depicted in FIGS. 1, 2, 6, 12 and 15 to 20.

At the distal end 176 of each of the side arms 154 and 156 there is a reinforcing ring 178 to provide a fixed size of aperture at the end of the side arm to allow expansion of a balloon inflatable or self expanding side arm extension stent graft within it to enable sealing at the aperture. The distal reinforcing ring 178 can be either a separate entity to the helical wire reinforcement, or integral with it.

It will be particularly noted in FIG. 27 that the zig zag stent 168 which is positioned in the region of the side branches has bends 178 and 180 respectively which are stitched to the bases 182 and 184 of the side arms 154 and 156. As the stent 168, like the other stents, is a resilient self expanding stent the bends 178 and 180 will tend to extend radially outwards which will assist with opening out the openings to the side arms within the stent graft 150 which in turn will facilitate catheterisation of the side arms.

The stent graft depicted in FIGS. 26 and 27 would normally have a diameter of the main tubular body of 12 mm to 16 mm and a diameter of the side arm of 6 to 8 mm. The side arms could each have a length of from 12 mm to 40 mm.

In FIG. 26 the helically or circumferentially crimped biocompatible graft material side arms 154 and 156 have the helical reinforcing wire 174 affixed to the graft material by means of a suture 177 stitched to the graft material and over the wire 174.

In FIG. 27 the helically or circumferentially crimped biocompatible graft material side arms 154 and 156 have the helical reinforcing wire 174 affixed to the graft material by means of a polyurethane adhesive 179 such as Thoralon®.

The stent grafts described herein may be delivered and deployed in a body vessel, such as the aorta, using the introducer described in U.S. Patent Application Publication 2006/0004433, "Thoracic Deployment Device and Stent Graft," which was filed on Jun. 15, 2005, and is hereby incorporated by reference. Preferably, the introducer includes a stent graft retention and release mechanism to allow selective release of each end of the stent graft. For example, the stent graft may be retained on the introducer by retention elements, such as a series of diameter-reducing ties or tethers (e.g., loops of suture material) that traverse the circumference of the graft. The retention elements may be in communication with trigger wires that allow for tightening or release of the respective devices by manipulation of a handle disposed outside the body. Suitable trigger wire systems are described in U.S. Patent Application Publication 2003/0233140, "Trigger Wire System," which was filed on May 29, 2003 and is hereby incorporated by reference. The stent graft may include tethers at the proximal and distal ends of the stent graft, as well as in the central portion of the stent graft. A top cap also may overlie the proximal end of the device.

The retention elements can be released in a predetermined order to deploy the graft. For example, tethers disposed at the proximal end of the stent graft are preferably released before tethers at the distal end to allow for adjustment of the length and position of the stent graft across the aneurysm or dissection before fully deploying the graft. Accordingly, the stent graft may be deployed in a gradual and controlled fashion along the length of the device, as shown schematically in FIGS. 28A-28C.

Figure 28A:
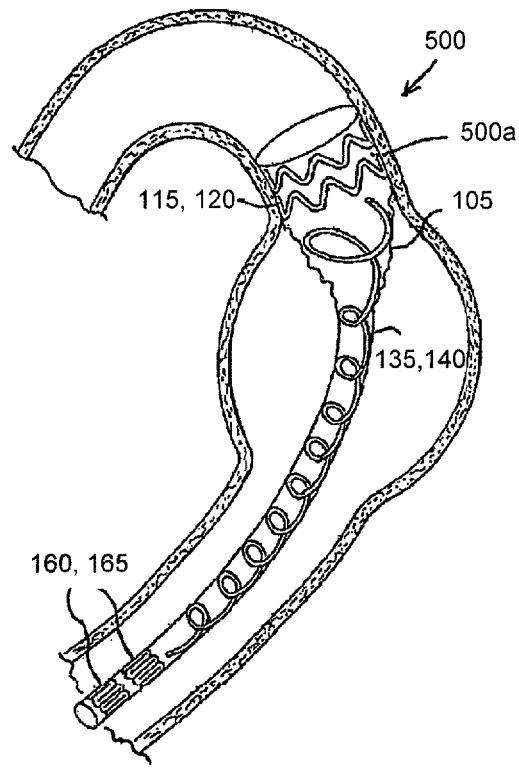
FIGS. 28A-28C show schematically a stent graft according to the first embodiment undergoing deployment at the site of an aneurysm.
Figure 28B:
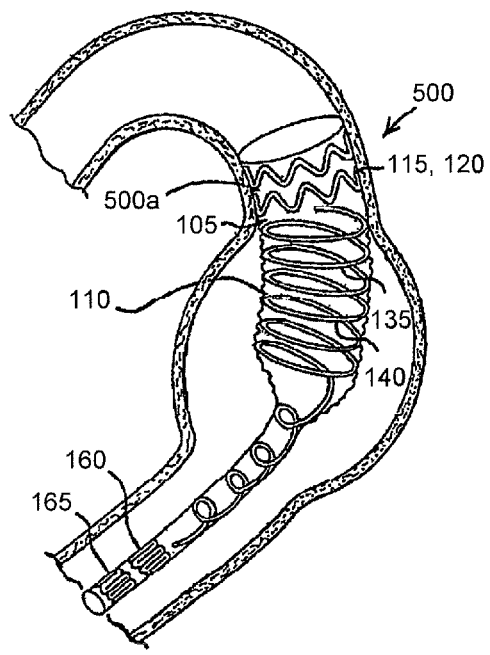
Figure 28C:
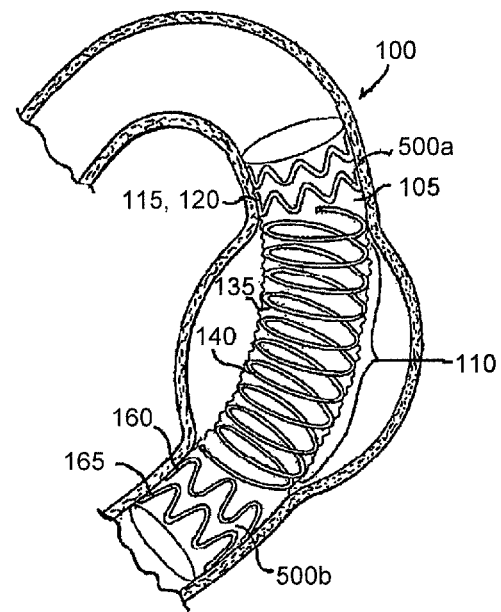

An exemplary deployment procedure may include insertion of the introducer, which includes the tethered stent graft, an overlying outer sheath and an underlying inner catheter, into a small incision in the groin to access the patient's femoral artery. Alternatively, access to the aorta may be achieved through other vessels, such as the carotid artery or an artery in the arm or abdomen. The stent graft is then directed under fluoroscopic guidance to the weakened or damaged section of the thoracic aorta. The outer sheath is retracted to expose the tethered stent graft. The proximal (top) portion of the stent graft may be maneuvered into the desired position, and the tethers securing the proximal portion may be released using the appropriate trigger wire, thus deploying the proximal end 500a of the graft 500, as shown in FIG. 28A. The tethers securing the central portion 110 of the stent graft 500 also may be released to expand all or a part of the central portion 110, as illustrated in FIG. 28B. Exploiting the flexibility and expandability of the central portion 110 of the stent graft 500, as described herein according to several embodiments, the central portion 110 and distal end 110b of the stent graft may be properly positioned at the treatment site while the proximal end 500a remains fixed. Once the desired adjustments to the positioning of the stent graft have been made, the remaining retention elements may be released to deploy the distal end 500b of the stent graft 500, as indicated in FIG. 28C.

While various embodiments of the invention have been described, it will be apparent to those of ordinary skill in the art that many more embodiments and implementations are possible within the scope of the invention. Accordingly, the invention is not to be restricted except in light of the attached claims and their equivalents.

What is claimed:

1. A stent graft system for deployment within a body vessel at a treatment site, the stent graft comprising:
    a tubular main body of biocompatible grafting material having a proximal end, a distal end, a proximal opening, a bifurcation at the distal end of the tubular main body, at least two tubular limbs extending from the bifurcation, and a first stent system having a first configuration attached to the tubular main body;
    a first leg extension, separate from the main body and configured for attachment to one of the tubular limbs after deployment of the main body at the treatment site, the first leg extension comprising a tube of graft material having a proximal end, a distal end, a distal end opening, a length between the proximal and distal ends, and a plurality of predetermined circumferential crimps having alternating circumferential troughs and circumferential crests along the length of the graft material, and a second stent system having a second configuration different from the first configuration attached along the length of the graft material of the first leg extension, wherein the second configuration of the second stent system includes at least one circumferential turn of a wire attached to a first circumferential crest on an exterior surface of the tubular main body and disposed substantially circumferentially about the first circumferential crest;
    wherein the graft material of the first leg extension is configured to change in length during use.

2. The stent graft system of claim 1 wherein the first configuration comprises an undulating configuration.

3. The stent graft system of claim 2, wherein the second stent configuration does not include an undulating configuration.

4. The stent graft system of claim 1, wherein the tubular main body is uncrimped.

5. The stent graft system of claim 1 further comprising a second leg extension configured for attachment to the other of the tubular limbs, the second leg extension comprising a tube of graft material having a proximal end, a distal end, a length between the proximal and distal ends, and a plurality of predetermined circumferential crimps having alternating circumferential troughs and circumferential crests along the length of the graft material, and a third stent system having a third configuration different from the first configuration attached along the length of the graft material of the second leg extension, wherein the second stent configuration includes at least one circumferential turn of a wire attached to a first circumferential crest of the second leg extension and disposed substantially circumferentially about the first circumferential crest of the second leg extension;
    wherein the graft material of the second leg extension is configured to change in length during use.

6. The stent graft system of claim 5, wherein the third stent configuration of the second leg extension does not include an undulating configuration.

7. The stent graft of claim 1 wherein first leg extension includes a reinforcing ring its distal end.

8. The stent system of claim 1 further comprising a second turn of a wire attached to and substantially circumferentially about a second circumferential crest.

9. The stent graft of claim 1, wherein each of the circumferential crests has a substantially circumferential length of wire attached to and about the circumferential crest.

10. A flexible stent graft for deployment within a body vessel at a treatment site, comprising:
    a tubular body, having a first end, a first end opening, a second end, a second end opening;
    a tube of graft material, the graft material comprises a plurality of predetermined circumferential or helical crimps having alternating troughs and crests along a length of the graft material, the graft material thereby configured to change in length during use; and
    a coiled stent including a plurality of helical turns with spacings between the turns, the coned stent being affixed to an exterior of the graft material by sutures stitched to the graft material and over the coiled stent,
    the stent graft having a diameter and the coiled stent comprising a helix diameter substantially the same as the stent graft diameter, the coiled stent comprising a ratio of helical pitch to helix diameter of from about 1:5 to about 1:10, the helical pitch being the spacing between adjacent turns of the coiled stent;
    wherein the tube of graft material is configured to extend an amount corresponding to about 5%-100% of an unextended length thereof; and
    wherein the helical turns of the coiled stent are received in the troughs of the graft material.

11. The stent graft of claim 10, further comprising a reinforcing ring about the first end opening of stent graft.

12. The stent graft of claim 10, further comprising a reinforcing ring about the second end opening.

13. The stent graft of claim 10 wherein the helical turns of the coiled stent are disposed on and stitched to the crests of the graft material.

14. The stent graft of claim 10 wherein the helix diameter is in the range of from 6 mm to 36 mm, and the pitch length is from 2 mm to 10 mm.

15. A flexible stent graft for deployment within a body vessel at a treatment site, comprising:
    a tubular body, having a first open end, a second open end;
    a tube of graft material, the graft material comprises a plurality of predetermined circumferential or helical crimps having alternating troughs and crests along a length of the graft material, the graft material thereby configured to change in length during use; and
    a coiled stent including a plurality of helical turns with spacings between the turns, the coiled stent being affixed to an exterior of the graft material by sutures stitched to the graft material and over the coiled stent,
    the tube of graft material having a diameter and the coiled stent comprising a helix diameter substantially the same as the tube of graft material diameter, the coiled stent comprising a ratio of helical pitch to helix diameter of from about 1:2 to about 1:20, the helical pitch being the spacing between adjacent turns of the coiled stent;
    wherein the tube of graft material includes a non-undulating reinforcing ring disposed about an open end thereof.

* * * * *